United States Patent
Francescatti et al.

(10) Patent No.: US 7,914,434 B2
(45) Date of Patent: Mar. 29, 2011

(54) ENDOSCOPIC/PERCUTANEOUS ELECTRONIC RADIATION APPLICATOR AND METHOD OF USE

(75) Inventors: Darius Francescatti, Barrington, IL (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 0 days.

(21) Appl. No.: 11/481,242

(22) Filed: Jul. 3, 2006

(65) Prior Publication Data

US 2008/0004524 A1    Jan. 3, 2008

(51) Int. Cl.
 *A61N 5/00*    (2006.01)
(52) U.S. Cl. .......................................... 600/3
(58) Field of Classification Search .................. 600/1–8, 600/101, 427; 378/65; 606/13, 16, 17; 604/20, 604/21, 103.01
See application file for complete search history.

(56) References Cited

U.S. PATENT DOCUMENTS

| | | | |
|---|---|---|---|
| 5,452,720 A | 9/1995 | Smith et al. | |
| 6,095,966 A | 8/2000 | Chornenky et al. | |
| 6,241,670 B1 * | 6/2001 | Nambu | 600/427 |
| 6,319,188 B1 | 11/2001 | Lovoi | |
| 6,496,561 B1 * | 12/2002 | Meyer et al. | 378/65 |
| 6,556,651 B1 | 4/2003 | Thomson et al. | |
| 2003/0149327 A1 | 8/2003 | Chin et al. | |
| 2003/0191459 A1 * | 10/2003 | Ganz et al. | 606/15 |
| 2005/0065504 A1 * | 3/2005 | Melsky et al. | 606/16 |
| 2005/0101825 A1 | 5/2005 | Winkler et al. | |
| 2008/0009659 A1 | 1/2008 | Smith et al. | |
| 2008/0043903 A1 * | 2/2008 | Yin et al. | 378/21 |

* cited by examiner

*Primary Examiner* — Charles A Marmor, II
*Assistant Examiner* — Christine D Hopkins
(74) *Attorney, Agent, or Firm* — Thomas M. Freiburger

(57) ABSTRACT

Treatment of lesions in any luminal or organ system of mammalian anatomy is performed using an electronic source of ionizing radiation and aided by an endoscopic or percutaneous approach.

28 Claims, 3 Drawing Sheets

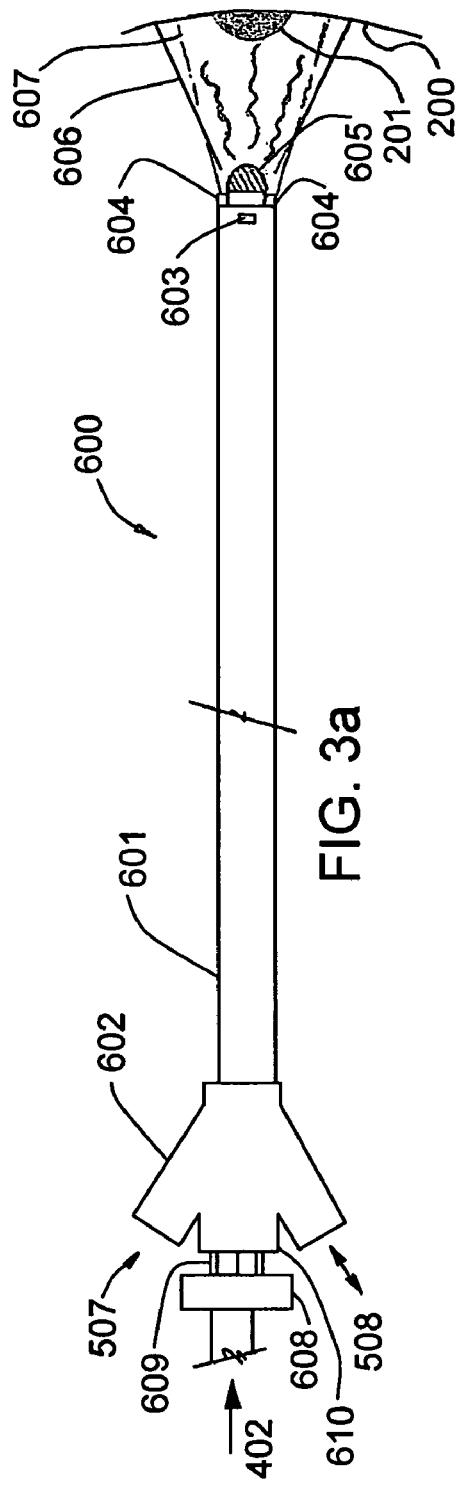
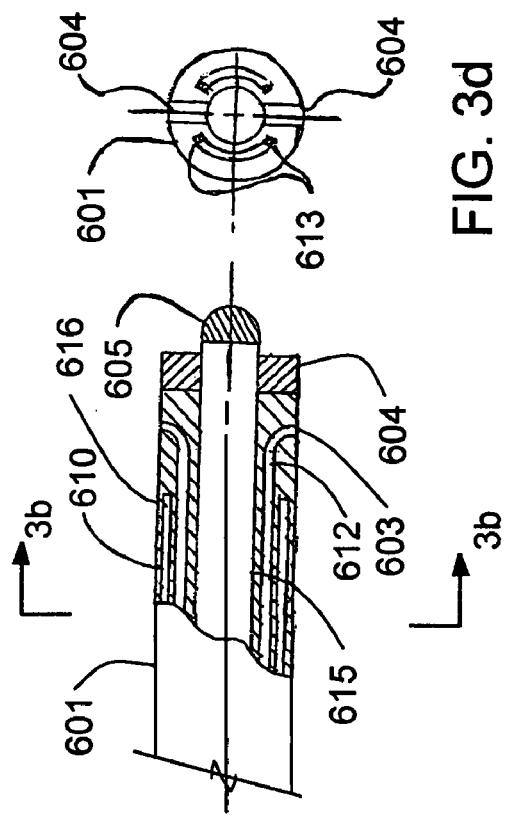
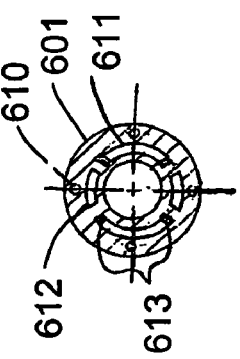
FIG. 3a
FIG. 3b
FIG. 3c
FIG. 3d

ENDOSCOPIC/PERCUTANEOUS ELECTRONIC RADIATION APPLICATOR AND METHOD OF USE

BACKGROUND OF THE INVENTION

This invention is concerned with therapeutic irradiation of lesions in organs or lumina of mammalian patients, especially humans.

Therapeutic delivery of radiation therapy to many organs, lumina, and systems within the body using radioactive isotopes is well known. Presently, radiation therapy is directed to tissue within an organ system of the body that permits the introduction of the device to both target and treat; examples of routes that could be used are the gastrointestinal tract and all its tributaries, i.e. the common duct hepatic duct and the pancreatic duct, the urinary tract and its tributaries, i.e. the urethra and ureter providing access to the kidney and all distal organ systems of the urinary tract, the vascular system including the lymphatic system, which will provide access to any organ system in the body including the integument, the neurological, the endocrine, the pulmonary, the musculoskeletal and the hematopoietic systems. This list should not be considered complete because of other points of access to all areas of the body via a percutaneous or transvisceral route specific portions of the alimentary, biliary, vascular, neurological, gynecologic, and urinary systems. Traditionally, therapeutic radiation is generated by large units operating outside the patient and is a beam of radiation directed to specific anatomy. If the beam is omni directional, shielding of non-diseased areas adjacent to the anatomy to be treated is required. In order to avoid damaging exposure to areas of the patient's skin and other tissue leading to the target region, multiple beams of radiation may be directionally administered so as to intersect at the lesion or abnormality being treated. These beams may be applied simultaneously or sequentially, such that the prescribed dose is applied to the tumor, but lesser radiation is applied to normal tissue. Irradiation using such intersecting, externally-applied beams is sometimes known as intensity modulated radiation therapy, or IMRT.

In some instances, radioisotopes are used within organs and lumina within the body in an effort to more directly treat diseased tissue. Because of the isotropic nature of the radiation emitted by radioisotopes, however, present methods of internal treatment may require the therapist to compromise in preparing treatment plans in order to prevent damage to normal tissue adjacent to the target lesions, but still effectively treat the lesion. The potential for serious complications exists. Thus, treatment of the abnormalities is often times compromised resulting in less than optimal therapy to the tumor itself. In addition, use of radioisotopes has attendant radiation safety concerns for therapeutic personnel. The practical effect of these limitations and concerns is that both externally and internally applied treatment modalities lack optimal targeting specificity, and are less focused on the tumor than desired. As a consequence, normal tissue is damaged.

In view of the shortcomings of the methods described above, there is a need for apparatus and methodology for delivery of a controllable, more finely focused radiation therapy. It is therefore an object of this invention to enable the therapist the ability to accurately direct the radiation therapy at the lesion according to an optimal plan, either by manual control of the radiation source, aided by direct visualization of the target area during the treatment process, or by using automated control methods. It is a further object of this invention that radiation risk to both the therapist and the patient be minimized during the treatment process.

SUMMARY OF THE INVENTION

Small electronic x-ray radiation sources are known (for example those disclosed in U.S. Pat. No. 6,319,188, the specification of which is incorporated herein in its entirety by reference) and along with their methods of use, comprise a part of this invention. Using an electronic radiation source, penetration depth can be controlled and the therapeutic radiation field can be limited or shaped. With control of the radiation beam as described below and, with this invention, direct visualization or imaging assures that the target lesion is treated while essentially avoiding injury to normal tissue or structure adjacent to the lesion. If desired, the control of radiation exposure to normal tissue within or adjacent to the operative site can be provided by methods other than by visualization, for example by endoscopically positioned radiation shielding. See, for example, copending application Ser. No. 11/471,277, the disclosure of which is incorporated herein by reference. Unlike the typical isotope radiation used therapeutically, electronically generated, low intensity x-ray radiation is effectively attenuated by positioning even modest shielding material over the areas to be protected.

Both rigid and flexible catheter, laparoscopic, and endoscopic apparatus and methods of use exist which comprise fiber optic or other methods to illuminate the operative field and coherent fiber optic bundle or camera means wherein the therapist is able to view his field, either by looking through a lens or by observing his field on a monitor driven by inputs from within the patient. Since such catheters and endoscopes often comprise fiber optic bundles, it is a simple matter using conventional methods to assign optic channels for visual light markers directed at the point of incidence of the x-rays onto tissue. For example, this marker might comprise an "X" at the point of incidence. With such markers, the surgeon can visually aim his beam at the target tissues for which treatment is prescribed.

Many such endoscopes or laparoscopes additionally include operating channels through which instruments can pass into the operative field. Through such an endoscope operating channel, an instrument can be both accurately aimed and manipulated or actuated under direct or monitored visualization by manipulating the endoscope. Such an instrument might comprise a wand or catheter with an electronic radiation source at or near its distal extremity, and which may easily pass through the working channel or an auxiliary entry port. If desired, such a radiation source can have a narrowly directed beam. The shaft of the instrument can also comprise lumina for flushing and suctioning the operative site. As an alternative to flushing and suction functionality in the endoscope, the catheter itself may be fashioned with lumina to provide such functionality.

Some visualization means currently used in minimally-invasive surgery comprise a semiconductor chip camera (CCD or CMOS device) which is very small, and which can communicate outside the patient's body for visualization of the field by either wire or wireless means. Such a camera, along with illumination and other optional features including those mentioned above, can all be incorporated into a radiation source catheter, thus integrating the functions of the endoscope and the radio-therapy catheter into one device. Such integration can result in a smaller device than a conventional endoscope adequate to accommodate a source catheter and its associated systems.

Armed with one of the devices as described above, a minimally-invasive radiation therapist can gain access to any lesion which is within an organ system of the body that permits the introduction of the device to both target and treat the lesion or other abnormality. Examples of access routes that can be used comprise the gastrointestinal tract and all its tributaries, i.e. the common duct, hepatic duct and the pancreatic duct, the urinary tract and its tributaries, i.e. the urethra and ureter providing access to the kidney and all distal organ systems of the urinary tract, the vascular system including the lymphatic system, which will provide access to any organ system in the body including the integument, the neurological, the endocrine, the pulmonary, the musculoskeletal and the hematopoietic systems. In addition, known methods of percutaneous or transvisceral access can be utilized, either through natural anatomic entrances into body, or by percutaneous access using known methods. A planned dose of therapeutic radiation can therefore be delivered accurately to any abnormality amenable to radiation as a form of curative or palliative treatment. Since the radiation field is controllable, and since risk of inadvertent radiation exposure to the patient and therapeutic personnel can be easily minimized, safe and controlled targeting of tissue under direct vision is possible with minimal protective measures.

The invention is applicable with endoscopes, laparoscopes, catheters and similar access devices, although the word endoscope is primarily used in the following description. The word endoscope is to be understood as including any such shaft device for extending deeply into a patient's anatomy, percutaneously or through a natural anatomical entrance, and with viewing or placement-confirmation capability.

DESCRIPTION OF THE DRAWINGS

FIG. 3a is a side view of an integrated embodiment of the invention comprising an x-ray source, imaging, targeting, flush and suction functionality, steer-ability, and illumination in one device.

FIG. 3b is a cross-sectional view through the shaft of the embodiment of FIG. 3a.

FIG. 3c is a partially sectioned side view of the tip of the embodiment of FIG. 3a.

FIG. 3d is a distal end view of the tip of the embodiment of FIG. 3a.

DESCRIPTION OF PREFERRED EMBODIMENTS

Figure 1:
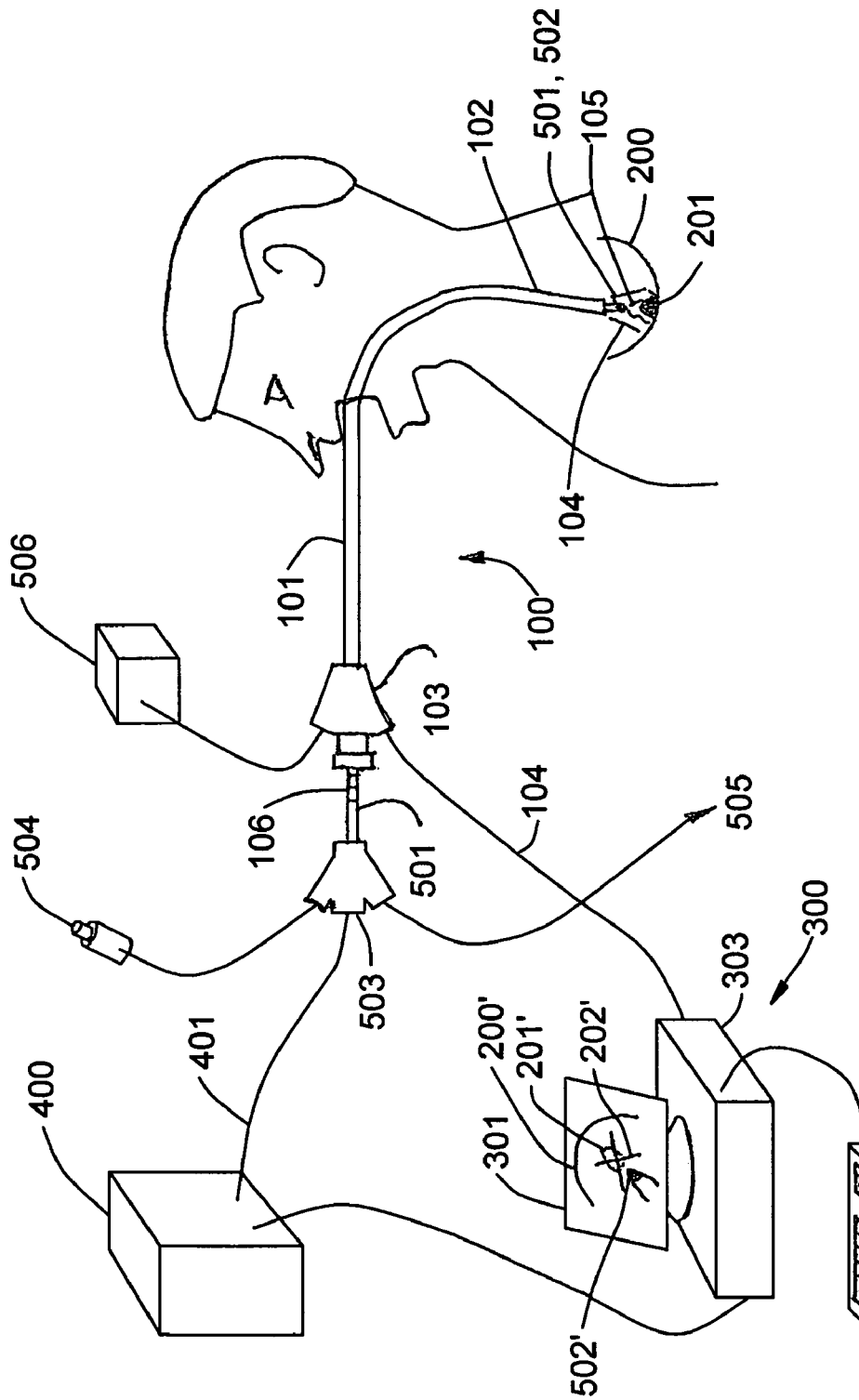
FIG. 1 shows a system of the invention schematically in relation to a patient.

FIG. 1 shows a system 100 comprising an endoscope 101 with a flexible shaft 102, and having at its distal tip, provision for lighting the operative field 200 and the tumor 201. Light is provided by light source 506. The endoscope 101 also comprises imaging apparatus and transmission means to enable viewing of the operative field 200 and the tumor 201 on a monitor 301 (tumor shown as 201'). Note the target "X" 202' superimposed on tumor image 201', and source 502' on field image 200'. An image transmission means 104 can be by a conductor or conductors, coherent fiber optic bundle, or by wireless transmission to a processor 303, of which the monitor 301 is a part. A camera can be located at the distal end, as discussed below. A keyboard, tablet, voice activated or other input device 302 completes processor system 300.

Within the endoscope 101 is a radiation source catheter 501, having a miniature x-ray tube 502 at its distal tip and a hub 503 at its proximal end. The power supply 400 provides power to drive the x-ray tube 502 through a power connection cable 401. The radiation source 502 has a distally directed radiation beam 105, such that radiation beam can be directed onto tumor 201 by manipulating the distal tip of endoscope 101 within the operating field. Alternatively, the beam can be directed elsewhere. At the proximal end of the catheter 501 is the catheter hub 503. The hub comprises a connection to the power cable 401 coming from the power supply 400 to drive the x-ray tube, a connection to the on/off switch 504, and an optional suction, flush or vent system 505 connection communicating with the distal tip of the catheter 501, as described above.

The endoscope 100 generally has a flexible section which can be steered as desired by the therapist. The endoscope has a hub 103 at its proximal end, the controls of which can be used to manipulate the direction in which the distal tip is directed, and hence the catheter tip and/or visualization apparatus. Such controls are well understood by those of skill in the art, and are therefore not detailed here. By hand manipulation of the endoscope, the lesion can be illuminated and targeted, and by advancing or withdrawing the catheter 501, the distance from the radiation source 502 to the lesion 201 can be optimized for therapeutic effect. Because visualization methods such as those described often lack the means to provide depth perception, the catheter may be advanced to touch a visualized surface within the operative field, then withdrawn a calculated distance for free beam targeting at optimal range. Graduated marks 106 can be provided on the catheter shaft at or about the endoscope hub 103 to facilitate this procedure.

The input device (keyboard, tablet or voice-actuated device) 302 is used to input prescription dose parameters for the x-ray source 502 into the processor 303. The processor 303 computes input voltage and current (and if required, laser light) parameters corresponding to the prescription, and commands the power source 400 as necessary to produce the prescribed dose. During therapy, a manual switch 504 emanating from the catheter hub 503 is used to control whether the source 502 is powered and active. Preferably, the switch 504 is normally open (switching radiation off when untended) such that radiation is only emitted while the therapist manually closes the switch. If desired, the source catheter 501 or endoscope 101 may include a lumen or lumina connected to a circuit 505 connected to a suitable receptacle (not shown) to vent, flush or suction the operative field.

If a greater degree of automation is desired, the apparatus and system may further comprise optical recognition methodology as described in co-pending patent application Ser. No. 60/742,118 filed Dec. 2, 2005, the specification of which is included by reference herein in its entirety. The processor system may then optionally comprise a timer and audible signaling device, for example a buzzer, to indicate to the therapist when the prescribed dose has been delivered. This is accomplished by cumulatively tracking delivered dose intensity over time. By comparing the real-time cumulative dose with a prescribed treatment plan and prescription dose information entered into the processor, verification of treatment to prescription can be accomplished and radiation emission may then be terminated. This system eliminates treatment beyond defined lesion boundaries as determined by the therapist, and can further modulate dose intensity within the treatment area.

Figure 2:
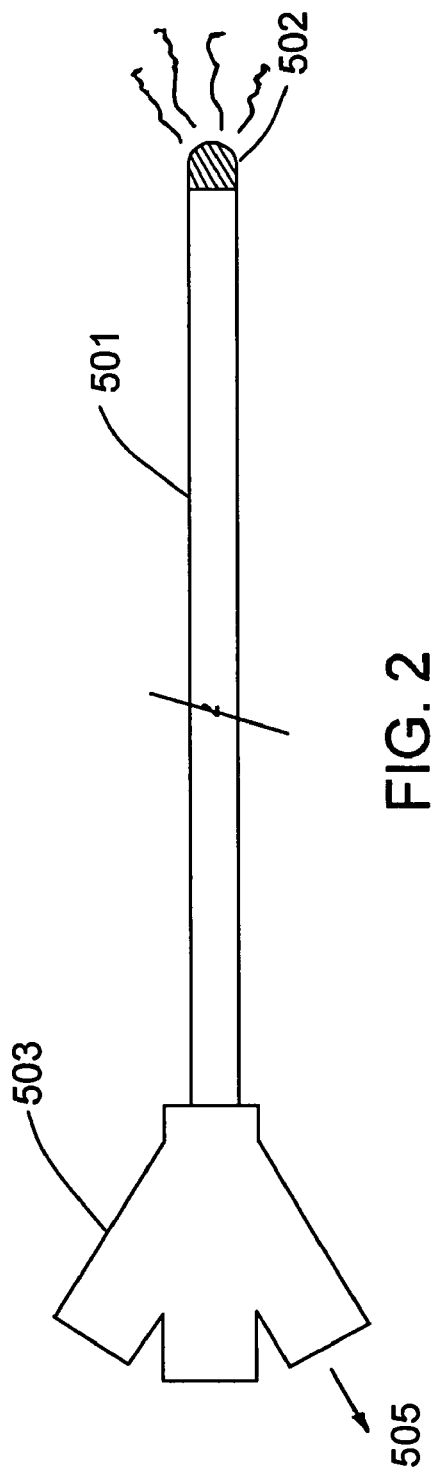
FIG. 2 is a side view of a catheter with a miniature x-ray source at it distal tip.

FIG. 2 shows a catheter 501 incorporating a miniature radiation source 502 at its distal tip. Miniature x-ray sources are described in U.S. Pat. No. 6,319,188, but in general consist of a flexible, high-voltage cable connected to a power source and controller at its proximal end and to the small x-ray tube at its distal end. The x-ray tube has a cathode (not shown) preferably at its proximal end, which can be caused to emit electrons (for example by heat) and a target anode (not shown) at its distal end. The voltage between the cathode and anode causes acceleration of the electrons emitted by the cathode past the anode, where they next impinge on the target, resulting in bremsstrahlung, or in this case, the creation of x-rays. The spectrum of energies produced is related to the voltage applied between the cathode and anode and the target material used. It is this variable voltage that can be used to control the penetration depth into tissue of the emitted X rays.

FIGS. 3a through 3d depict a single device with all functionalities described above combined into one device embodiment. Other functionality could be included or substituted. Device 600 shown in FIG. 3a, which can be called an endoscope with onboard x-ray source, comprises a shaft 601 having a central lumen for a source catheter 615 having an x-ray source 605 at its distal tip. The source 605 is positioned at or near the distal end of the shaft 601. At the proximal end of the shaft 601 is a conventional hub 602, comprising a central port 610 to accommodate the source catheter 615 (FIG. 3c) and the necessary sub-systems 402 to support operation of the source 605. These systems may include filament current or laser energy to activate the cathode, accelerating voltage, and fluid flow for cooling. A lower auxiliary port 508 is provided for flushing and suction, and an upper port 507 for light input for illumination and targeting. Just proximal of hub 602 is a sort of swash plate 608 for manipulating the wires 609 (of which there are at least two for planar manipulation or three for spatial manipulation) for bending the flexible section or sections of the shaft 601, i.e. bonding the endoscope. The wires act in a coordinated, push-pull manner. These wires 609 pass through lumina in the shaft 601 (see FIG. 3b) but are anchored at their distal ends which are positioned at the distal extreme of the flexible shaft portion 616 of the shaft 601 in FIG. 3c. FIG. 3b shows the lumina 610 for the wires 609, as well as lumina 612 for flushing and suction. These fluid lumina 612 terminate proximally in the port 508 where they are connected conventionally to fluid source and evacuation systems in the operating room. Lumina 612 terminate at ports 603 (see FIGS. 3a, 3c) near the distal tip of shaft 601. FIG. 3b also shows lumina 611 for fiber optic bundles for illumination, and optionally for targeting. Proximally, these lumina 611 terminate in port 507 where they are conventionally connected to a light source or sources, such as is shown in FIG. 1 as light source 506. Distally, these fibers terminate at the end of the shaft 601 and provide an illumination cone 606 (solid line cone in FIG. 3d).

Targeting is accomplished by edge fibers 613 positioned at the circumferential extremes of lumina 611. (See FIGS. 3b, 3d.) These fibers 613 transmit colored light which preferably contrasts with the operative field (for example, green light). Their distal ends are beveled or otherwise shaped so as to provide a useful, visible target 202, locating the direction of emitted x-rays for the therapist. (Note the "X" shaped image 202' on the monitor screen in FIG. 1). The target shape is arbitrary.

Adjacent to the source 605 at the distal tip of shaft 601 are two chip cameras 604 in diametrically opposed positions. With this arrangement, stereoscopic visualization is provided through a visualization cone 607 (phantom line cone in FIG. 3d). Alternatively, one camera, or a coherent fiber bundle can be substituted for these cameras 604. Such a coherent bundle could pass through the shaft 601 through lumina 611.

Although the above describes a source-bearing catheter positioned in a lumen of an endoscope or device, the construction can be otherwise and more integral. With the x-ray source 605 at the distal end of the device, the shaft 601 can be constructed in various ways, so long as the source 605 is supported by adequate dielectric and standoff spacing for high-voltage conductors leading through the shaft. The dielectric material can be formed solidly and fixedly in the center of the endoscope 600. The entire shaft 601 or endoscope 600 could be of dielectric material, with conductors adequately spaced and not necessarily in the central space described as a lumen with catheter 615 in FIGS. 3a-3d.

The miniature electronic x-ray source 502, 605 described in connection with an endoscope has great advantages over treatment with isotope radiation.

Radiation from radioisotopes is emitted in a known manner with a decaying intensity measured by the isotope's half-life—the time at which half the original intensity remains. Within practical time constraints, these parameters for a given radioisotope are fixed and they cannot be altered thus offering no possibilities for control. Furthermore, radioisotopes emit radiation at a few distinct energy bands, radiation from each band having its own ability to penetrate tissue and deliver dose. For example, the high-energy band of radiation emitted from $^{192}$Ir, the most common high dose-rate brachytherapy isotope, penetrates through large thicknesses of shielding materials. In addition, isotopes are always "on", so controlling the output with on/off switching is not possible. Other common medically relevant radioisotopes also have emission spectra containing high energy components that make selective shielding within a body cavity impractical due to space considerations. The radiation from these isotopes will penetrate any practical thickness of shielding material. This high-energy radiation easily penetrates well beyond the target site requiring therapy, thus delivering radiation to healthy parts of the body and risks injury.

In contrast, with electronically controlled radiation sources, the shape of the anode and its structure, and any minimal shielding utilized, determines the directionality of the x-rays emitted. The emitted x-rays may be emitted isotropically, they may be directed radially, axially, or a combination thereof. Anode shaping is well known by those skilled in the art of x-ray generation apparatus. Anode shape, target thickness and target configuration can be used to change the radiation profile emitted from the miniature x-ray source. For low energy miniature x-ray sources, thin radiation shields can easily produce directional radiation. For electronically produced x-rays, the acceleration voltage determines the energy spectrum of the resulting x-rays. The penetration of the x-rays in tissue is directly related to the energy of the x-rays. The cumulative radiation dose directed at a point of the lesion may be controlled by x-ray source beam current or "on" time within the body of the patient.

In using the system of the preferred embodiment, the therapist enters the desired prescription dose into the processor system 300. The processor computes power parameters and transmits those to the power supply 400. The therapist then positions the endoscope 100 within the anatomical cavity in which the treatment is to take place, and if necessary, performs flushing and/or suctioning to prepare the treatment field. This can be done under direct visualization. Next, and if needed, the therapist can verify calibration of the radiation source using an ion chamber or similar device. Then, the radiation catheter 501 is introduced and positioned to treat the lesion, both by use of the endoscope controls and by advancing the catheter 501 to achieve the proper treatment range between the tip of the source and the lesion. When ready to proceed with the treatment, the therapist closes the switch 504, continually or intermittently as desired, until the processor alarm sounds (or total time is determined by other means) at which point the switch 504 is opened (released), concluding the treatment. As previously described, some of these steps may be wholly or partially automated.

Although this embodiment is discussed with particular reference to endoscopic practice, similar methods can be utilized with either laparoscopic or catheter methods without departing from the scope of the invention. References to endoscope or endoscopic in the claims is to be taken as referring to any of those instruments and methods.

The above-described preferred embodiments are intended to illustrate the invention, but not to limit its scope. Other embodiments and variations to these preferred embodiments will be apparent to those of skill in the art and may be made without departing from the spirit and scope of the invention.

What is claimed is:

1. A method for treating cancerous lesions in the stomach or gastrointestinal tract of a patient, comprising:
    inserting an endoscope into the patient, to extend the distal end of the endoscope to the stomach or gastrointestinal tract within the patient's body adjacent to a cancerous lesion or tumor or to be treated by irradiation, while using the endoscope to visualize placement of the distal end,
    inserting into a lumen of the endoscope a catheter having at its distal end an electronic x-ray source which is controllable as to voltage and thus x-ray penetration depth, to a position at which the x-ray source is adjacent to the lesion to be irradiated, the x-ray source being connected to a controller, wherein the catheter and x-ray source are connected to a power supply and a processor, the processor having an input device and including the operator's entry of data relating to the desired irradiation of the patient's lesion, with the processor calculating a treatment plan including voltage settings and time duration of irradiation, such that when the electronic x-ray source is switched on the voltage and duration of irradiation are controlled by the power supply and the processor, and
    switching on the x-ray source and, using the controller to set the x-ray source voltage at a selected level in accordance with a prescription dose and a treatment plan, and carefully controlling position of the distal end of the endoscope and the x-ray source by visualization using the endoscope, treating the patient's lesion with radiation delivered directly from the x-ray source and specifically at the lesion until substantially a desired dose of radiation has been delivered to the lesion.

2. The method of claim 1, wherein the endoscope further includes a suction channel, and including suctioning out liquid adjacent to the lesion prior to irradiating.

3. The method of claim 1, wherein the catheter further includes a suction channel, and including suctioning out liquid adjacent to the lesion prior to irradiating.

4. The method of claim 2, further including flushing the site of the lesion through the endoscope prior to suctioning.

5. The method of claim 3, further including flushing the site of the lesion through the catheter prior to suctioning.

6. The method of claim 5, wherein the steps of flushing and suctioning are performed under direct visualization by the operator using the endoscope.

7. The method of claim 1, wherein the controller includes a momentary switch for the use by an operator to control on/off status of the electronic x-ray source.

8. The method of claim 7, wherein the momentary switch is positioned near the proximal end of the catheter.

9. The method of claim 1, wherein the electronic x-ray source in the catheter is capable of emitting radiation in different selected rotational positions, and the method including rotating the emitted field of radiation from the x-ray source as a patient is treated.

10. The method of claim 9, further including varying the x-ray source voltage and thus depth of penetration of the radiation for different rotational positions, of the field of radiation.

11. The method of claim 1, wherein the endoscope includes
a. camera at the distal end of the endoscope, and including the step of viewing a monitor that displays live images from the camera, to view the patient's tissue and the lesion as the patient is treated.

12. The method of claim 11, including a light source on the distal end of the endoscope for illuminating the patient's tissue.

13. The method of claim 1, wherein the endoscope includes at its distal end a light source and a camera, the light source being positioned to illuminate the field of radiation on the tissue and the method including an operator's viewing the tissue on a monitor connected to the camera.

14. The method of claim 1, wherein the x-ray source is distally directed from the catheter.

15. The method of claim 1, wherein the x-ray source is side-looking from the catheter, emitting radiation in one direction only.

16. The method of claim 15, wherein the side-looking x-ray source is rotational under the control of the operator or the controller, and including rotating the source during treatment of the patient to rotationally sweep the field of radiation from the source.

17. The method of claim 16, wherein the x-ray source is translational distally/proximally as well as rotational, and including translating and rotating the source during a treatment.

18. The method of claim 1, wherein the endoscope is inserted into the patient percutaneously.

19. The method of claim 1, wherein the endoscope is inserted into the patient through a natural anatomic entrance.

20. A method for delivering radiation internally to a patient, comprising:
    inserting an endoscope into the patient, to extend the distal end of the endoscope to a cavity or space within the patient's body adjacent to a lesion, tumor or other lesion to be treated by irradiation, while using the endoscope to visualize placement of the distal end,
    inserting into a lumen of the endoscope a catheter having at its distal end an electronic x-ray source which is controllable as to voltage and thus x-ray penetration depth, to a position at which the x-ray source is adjacent to the lesion to be irradiated, the x-ray source being connected to a controller,
    placing dosimeters in or adjacent to the patient's tissue to be irradiated, and
    switching on the x-ray source and using the controller to set the x-ray source voltage at a selected level, treating the patient's lesion with radiation and, during treatment of the patient, feeding back dose information from the dosimeters to the controller to determine dose received at multiple points in the tissue, until substantially a desired dose of radiation has been delivered to the lesion.

21. The method of claim 20, wherein at least one of the dosimeters is inserted through the endoscope.

22. A method for treating cancerous lesions in the stomach or gastrointestinal tract of a patient, comprising:

inserting an endoscope into the patient, to extend the distal end of the endoscope to the stomach or gastrointestinal tract within the patient's body adjacent to a cancerous lesion or tumor to be treated by irradiation, while using the endoscope to visualize placement of the distal end, the endoscope including at its distal end an electronic x-ray source which is controllable as to voltage and thus x-ray penetration depth, the x-ray source being connected to a controller, wherein the x-ray source is connected to a power supply and a processor, the processor having an input device and including the operator's entry of data relating to the desired irradiation of the patient's lesion, with the processor calculating a treatment plan including voltage settings and time duration of irradiation, such that when the electronic x-ray source is switched on the voltage and duration of irradiation are controlled by the power supply and the processor, and switching on the x-ray source and, using the controller to set the x-ray source voltage at a selected level in accordance with a prescription dose and a treatment plan, and carefully controlling position of the distal end of the endoscope and the x-ray source by visualization using the endoscope, treating the patient's lesion with radiation delivered directly from the x-ray source and specifically at the lesion until substantially a desired dose of radiation has been delivered to the lesion.

23. The method of claim 22, wherein the endoscope further includes a suction channel, and including suctioning out liquid adjacent to the lesion prior to irradiating.

24. The method of claim 23, further including flushing the site of the lesion through the endoscope prior to suctioning.

25. The method of claim 22, wherein the electronic x-ray source is capable of emitting radiation in different selected rotational positions, and the method including rotating the emitted field of radiation from the x-ray source as a patient is treated.

26. The method of claim 25, further including varying the x-ray source voltage and thus depth of penetration of the radiation for different rotational positions of the field of radiation.

27. The method of claim 22, wherein the endoscope includes a camera at the distal end of the endoscope, and including the step of viewing a monitor that displays live images from the camera, to view the patient's tissue and the lesion as the patient is treated.

28. The method of claim 27, including a light source on the distal end of the endoscope for illuminating the patient's tissue.

* * * * *